United States Patent [19]

Kollar

[11] 3,985,795

[45] Oct. 12, 1976

[54] PROCESS FOR PREPARING GLYCOLS FROM THEIR ESTER PRECURSORS

[75] Inventor: John Kollar, Wyckoff, N.J.

[73] Assignee: Halcon International, Inc., New York, N.Y.

[22] Filed: Dec. 30, 1974

[21] Appl. No.: 537,298

Related U.S. Application Data

[63] Continuation of Ser. No. 16,259, March 3, 1970, abandoned.

[52] U.S. Cl. .......................... 260/497 R; 260/635 R
[51] Int. Cl.$^2$................. C07D 67/05; C07D 29/00
[58] Field of Search ................................ 260/497 R

[56] References Cited
UNITED STATES PATENTS

| 3,479,395 | 11/1969 | Huguet | 260/497 |
|---|---|---|---|
| 3,542,857 | 11/1970 | Lutz | 260/497 |

FOREIGN PATENTS OR APPLICATIONS

| 1,029,319 | 5/1966 | United Kingdom | 260/497 |

OTHER PUBLICATIONS

March, *Advanced Organic Chemistry*, p. 303 (1968).

Primary Examiner—Lorraine A. Weinberger
Assistant Examiner—Michael Shippen
Attorney, Agent, or Firm—William C. Long; David Dick; Riggs T. Stewart

[57] ABSTRACT

Glycol esters of an olefin are prepared by contacting an olefin and a molecular oxygen containing gas in a carboxylic acid medium in the presence of a catalyst. Selectivities to the desired glycol esters are improved by treating the viscous residue and the precursor light components separated from the oxidation effluent by contacting them with water. In a preferred embodiment both residue and precursor light components streams are fed to the same zone wherein they are converted to additional glycol.

10 Claims, No Drawings

PROCESS FOR PREPARING GLYCOLS FROM THEIR ESTER PRECURSORS

CROSS REFERENCES TO RELATED APPLICATIONS

This is a continuation of application Ser. No. 16,259 filed Mar. 3, 1970, now abandoned.

Applications closely related to the present invention and describing the particular catalytic reactions for producing glycol esters are co-pending applications, Ser. No. 763,001, filed Sept. 26, 1968, now abandoned, and Ser. No. 762,978, also filed Sept. 26, 1968, now abandoned.

BACKGROUND OF THE INVENTION

The co-pending applications disclose the catalytic systems employed in the oxidation reaction of the present invention. While these applications suggest how glycol esters of olefins may be produced, they do not disclose how the glycol esters may best be produced in a continuous fashion nor a method suitable for use on a commercial scale of operation.

Glycol esters and especially glycol carboxylic acid esters of olefins are particularly useful organic chemical intermediates and extractive solvents. The glycol esters of lower olefins, such as, ethylene are useful in the production of ethylene glycol, a chemical of enormous commercial importance. Ethylene glycol may be prepared by the hydrolysis of the ethylene glycol carboxylic acid esters as disclosed in co-pending application, Ser. No. 819,776, filed Apr. 28, 1969 now U.S. Pat. No. 3,647,892. Similarly, propylene glycol may be prepared by the hydrolysis of propylene glycol carboxylic acid esters.

Thus, despite the basic developments represented by the above co-pending applications, there still remains considerable room for further developments in the reaction system especially with a view to increasing the selectivity to the desired glycol esters.

Therefore, it is an object of the present invention to develop a process whereby glycol esters may be produced at improved selectivities.

It is also an object of the present invention to develop a process whereby the glycol esters may be prepared in a continuous fashion at improved selectivities.

SUMMARY OF THE INVENTION

In accordance with the present invention, it has been discovered that in the preparation of glycol esters from an olefin and a molecular oxygen containing gas in a carboxylic acid corresponding to the ester moiety in the presence of a catalyst comprising a variable valence metal cation and a halogen source, the liquid effluent from the oxidation zone contains a significant amount of high boiling residue and precursor light components produced during the oxidation reaction.

I have surprisingly found that these high boiling materials may be separated from the liquid reaction medium and then reacted with water where under oxidation temperatures they may be processed to yield additional amounts of the olefin glycol. Furthermore, I have discovered the precursor light components separated from the glycol esters may also be treated with water where they may be processed to yield yet further amounts of the olefin glycol.

By operating in the manner of my invention, I am able to increase oxidation selectivities to the desired glycol ester and especially to the glycol. This ability to operate at an increased selectivity to the glycol is most important when considering the normal commercial scale of operation.

The catalyst employed in the liquid phase reaction comprises a variable valent metal cation in conjunction with an appropriate halogen source. The halogen source is selected from the group consisting of bromine, chlorine, a bromine-containing compound and a chlorine-containing compound. The variable valent metal cation is selected from the group consisting of one or more of tellurium, cerium, antimony, manganese, vanadium, gallium, arsenic, cobalt, copper, selenium, chromium or silver.

DETAILED DESCRIPTION OF THE INVENTION

I have discovered that when an olefin and a molecular oxygen containing gas is intimately contacted with a liquid reaction medium comprising a lower carboxylic acid and a catalyst which comprises a variable valent metal cation and appropriate halogen source, significant quantities of a high boiling residue are present in the liquid effluent from the oxidation reaction. When this residue is separated from the liquid reaction medium it may be treated further to liberate the olefin glycol. This viscous liquid residue can be converted to the desired glycols by intimately contacting it with water at temperatures corresponding to the oxidation temperature. This residue includes all those hydrocarbon containing compounds which boil at a higher temperature than the desired ester and precursors. These ester precursors include the glycol monoester and the glycol. By the water treatment of this high boiling residue, which under normal oxidation conditions may contain up to about 30 mol percent of the reacted olefin, the selectivity of the oxidation can be increased significantly to the glycol.

Also readily separable from the desired glycol ester contained in the liquid effluent from the oxidation reactor are precursor light components. These precursor light components are defined as those hydrocarbon materials derived from the olefin and boiling at a lower temperature than the desired glycol ester and precursors. For example, in the case of ethylene oxidation to ethylene glycol diacetate, the precursor light materials contained in the oxidation effluent and derived from the ethylene include such materials as 1,2 dibromoethane or 1,2 dichloroethane, ethylene bromohydrin or ethylene chlorohydrin or 2-bromoethyl acetate or 2-chloroethyl acetate, depending on the halogen source used in the catalyst.

These light components may also be treated with water at oxidation temperatures to liberate additional olefin glycol. In a preferred embodiment they will be fed along with the residue to the same water zone where they are converted to the olefin glycol. Under preferred oxidation conditions, these light components may account for as much as 10 mol percent of the reacted olefin and upon the further water treatment of my invention aid in increasing oxidation selectivies to the glycol.

In the above discussion and throughout the specification, "selectivity" or "selectivity to the desired glycol ester" is meant the molar percentage of reacted olefin which forms the desired glycol diester or precursors. The precursors being the glycol monoester and glycol corresponding to the olefin. Thus, in the case of ethylene, the desired glycol ester product includes ethylene glycol diester, ethylene glycol monoester and ethylene glycol. Similarly, in the case of propylene, the desired glycol ester product includes propylene glycol diester, propylene glycol monoester and propylene glycol.

The olefins useful in the process of the invention are preferably the alkenes, ar-alkenes and cycloalkenes. Included among the alkenes are mono alkenes, di-alkenes, and tri-alkenes. The double bond in the mono alkene may be positioned at any one of the carbon atoms such as alpha, beta, gamma and delta positions and the like. Suitably, these alkenes are straight or branch chain containing from 2 to 30 carbon atoms.

More specifically, the alkenes may be lower alkenes of from 2 to 5 carbon atoms, intermediate alkenes of from 6 to 12 carbon atoms or higher alkenes of from 13 to 30 carbon atoms. Among the lower alkenes may be mentioned alkenes, such as, ethylene, propylene, butene -1, butene -2, 2-methylbutene -2, pentene -1 and the like. Specific intermediate alkenes, such as, tetradecen -1, pentadecene -1, hexadecene -1, pentacosene -1, and triacontene -1. Also contemplated are di-alkenes, tri-alkenes, ar-alkenes and cycloalkenes.

Among the di-alkenes the double bond may be conjugated or isolated and the carbon chain may be straight or branched wherein the double bonds are located in any desired position and the olefin may contain up to 30 carbon atoms. The ar-alkenes contemplated by this invention contain an aromatic nucleus with an alkenyl side chain as described above. The cycloalkenes of this invention are compounds containing from 5 to 15 carbon atoms in the nucleus and at least one double bond.

More specifically, the alkenes may be: lower mono alkenes of from 2 to 5 carbons, intermediate alkenes of from 6 to 12 carbons or higher alkenes of from 13 to 30 carbons. Among the lower alkenes may be mentioned alkenes such as ethylene, propene-1, allyl alcohol, butene-1, butene-2, 2-methylbutene-2, pentene-1 and the like. Among the intermediate alkenes may be mentioned heptene-2, octene-1 and decene-1 and among the higher alkenes, tetradecene-1, pentadecene-1, hexadecene-1, pentacosene-1 and triacontene-1. The lower di-alkenes may suitably contain up to 8 carbons, the intermediate alkenes 9 to 14 carbons and the higher alkenes 15 to 20 carbon atoms. Examples of these di-lower alkenes are 1,3-butadiene, 1,5-hexadiene, 1,4-pentadiene and 1,3-hexadiene.

More specifically, the ar-alkenes may be ar-lower alkenes such as phenyl alkenes and di-phenylalkenes wherein the alkenyl side chain may be any of those described above. Examples of such compounds are phenyl lower alkenes wherein the alkenes side chain contains from 2 to 5 carbons, such as styrene, 2-methyl styrene and alpha-ethyl-beta-methyl styrene and di-phenyl alkenes such as 1,1-di-phenylethylene, 1,2-diphenyl propene and 2,3-diphenylbut-2-ene.

More specifically, the cycloalkenes may be from 5–12 carbon atoms such as cyclopentene, cyclopentadiene, cyclohexene, cyclodocene and cyclododecene.

All of the above alkenes, ar-alkenes and cycloalkenes may contain one or more functional substituents which are inert to the reaction such as nitro, cyano, chloro, lower alkoxy (methoxy, propoxy), lower alkylthio (methylthio, butylthio) hydroxy, lower akanoyloxy of 2-6 carbons (acetyloxy) and the like.

In the more preferred aspects of this invention, the mono and di-lower alkenes, mono intermediate alkenes, mono higher alkenes, ar-lower alkenes and cycloalkenes are employed; and in its most preferred aspect ethylene, propylene, allyl alcohol, 1-3 butadiene, allyl acetate, allyl chloride, butene-2, methylbutene-2, decene-1, styrene and cyclohexene; but especially ethylene, propylene and butene-2 are employed.

The olefins contemplated by this invention may contain the variety of impurities normally associated with commercially available olefins. In addition, it is desirable to employ commercial olefins which contain inert materials normally associated with these olefins, such as propane in propylene. Furthermore, these inert materials may be employed in any desired ratio, and are preferably used in the various ratios are obtained from a variety of commercial source.

The carboxylic acids employed in the oxidation supply the ester moiety to the glycol ester are lower mono-aliphatic acids of from 2 to 6 carbon atoms such as acetic, propionic, butyric, isobutyric, the valeric and caproic acids as well as their substituted derivatives. Preferably, any substitutes are inert under the oxidation conditions. Also included with the scope of the invention are the dialiphatic acids of from 2 to 6 carbon atoms, such as, oxalic, malonic, succinic, glutaric and adipic. Preferably, the glycol esters to which the process of this invention is applicable includes ethylene and propylene glycol diacetate, diprionate, dibutyrate, diisobutyrate, divalerates, and dicaproates as well as the corresponding mono-esters.

The variable valent metal cation, if desired, may be utilized in its elemental form and added to the oxidation zone as a fine powder or may be added in any form which in solution under oxidation conditions will yield at least some soluble metal ions. For example, the metal source may be the carbonate, oxide, hydroxide, bromide, chloride, lower alkoxide (methoxide), phenoxide or metal carboxylate wherein the carboxylate ion is the same or different from the solvent anion. In its preferred aspect, the metal source is its oxide, hydroxide or salt of the acid solvent. Furthermore, the metal compound employed may contain impurities normally associated with the commercially available compounds, and need not be purified any further.

In the preferred oxidation systems, the variable valent metal cations are tellurium, cerium, antimony, manganese, vanadium, gallium, arsenic, cobalt, copper, selenium or silver when using a bromide source and more preferred is tellurium, cerium, antimony, manganese or vanadium and especially preferred is tellurium, cerium, antimony, and manganese. For use with a chloride source the preferred catalyst contains cerium, manganese, arsenic, cobalt, copper, selenium or chromium; the more preferred is cerium, manganese, cobalt, copper and selenium with the most preferred being cerium, manganese and cobalt.

The bromine or chlorine containing compound used in conjunction with the tellurium compound initially will be any compound capable of producing bromide or chloride ions in solution, under the oxidation conditions. For example, the most preferred forms are the hydrohalic acids, usually in concentrated form, or any metal or organic halide, provided, the cation of a metal halide salt does not impair the selectivity of the reaction to the desired glycol ester.

The various reactants employed in the oxidation reaction may be effectively used over a wide range of concentrations. The effective minimum concentrations of catalyst will depend upon temperature, residence time and the type of halogen expressed in weight percent of bromide or chlorine to total solution may be from 0.01% to 30% or higher, but preferably from 0.1% to about 20% and especially from about 0.5% to about 10%. The concentration of total operable tellurium cation present expressed in terms of equivalence of cation/equivalence of halogen expressed as bromine or chlorine may suitably vary from about 1:.01 to about 1:100 but preferably from about 1:0.2 to about 1:40 and especially from about 1:1 to about 1:20.

The mole ratio of oxygen to olefin in the feed is not critical and, therefore, any suitable mole ratio such as 1:100 to 1:.001 may be used; provided, of course, that the mixture used is not in the explosive region. The source of the oyxgen may be oxygen gas, or a mixture of oxygen and an inert gas such as found in air, or it may in fact be air.

The temperatures maintained in the oxidation zone may vary from about 50° C. to the bubble point of the liquid phase reaction mixture within the zone. However, the temperatures are preferably maintained between about 90° C. to about 180° C. The total pressure in the oxidation zone should be maintained at from about atmospheric or below to about 1000 psia. and preferably from about 25 psia. to about 1000 psia. Preferably, however, for the oxidation of lower olefins such as ethylene and propylene the total pressure of the oxidation zone should be maintained at from about 50 to about 1000 psia, and most preferably about 200 to about 500 psia. For the higher olefins, the pressure should be from about 25 to about 500 psia.

The time of reaction depends to a great extent upon the concentration of reactants and therefore, may suitably vary over a wide range. Flow rates are preferably adjusted so that the rate of formation of product as glycol diester is from about 0.10 to 10.0 gram-moles per liter - per hour. Once steady state conditions are obtained, the reaction can be continued with anywhere from about 5 to about 60% by weight of glycol ester products remaining in the liquid phase reaction medium, but this concentration is preferably maintained at from about 15 to about 50% by weight, based on the total weight of the liquid.

If desired, the reaction may be carried out in the presence of an inert solvent. Examples of such inert solvents are benzene, t-butylbenzene, t-butanol or ethylene glycol diacetate, etc. Preferably, however, the carboxylic acid is used as a solvent as well as the source of the acid moiety of the desired ester.

During the oxidation, a liquid product stream is continuously withdrawn from the oxidation zone. This stream comprising precursor light components, carboxylic acid, water, dissolved and suspended catalyst, glycol ester and precursors as well as the higher boiling materials which make up the residue, is subjected to a distillation to separate the higher boiling materials from the remainder of the stream. This first distillation may be a flash distillation carried out at from about 0.01 mmHg and 50° C. to about 760 mmHg and 220° C., but preferably from about 1 mmHg and 100° C. to about mmHg and 170° C. The residue is then contacted with water as described above.

The overhead or ligher fraction of the first distillation is subjected to a second stage distillation whereby product glycol ester and precursors are separated from the lower boiling compounds which include the precursor light components. During this distillation the glycol monoesters and glycols are almost completely esterified to the glycol diester. The product diester is then collected and treated depending on the desired end-product. The olefin derived light components are also separated and contacted with water as described above.

In the preferred operation of my invention at least one of the residue streams and the precursor light components stream is contacted with water after removal from the product stream. In the most preferred embodiment of the invention both precursor light components and residue, once separated from the oxidation effluent are contacted with water in the same zone.

The following Examples which are hereinafter submitted are intended for purposes of illustration of my invention and are not intended to be limitations on the scope of my invention. All percentages given are by weight unless otherwise specified.

EXAMPLE I

Into a 1.5 liter stirred titanium autoclave equipped with liquid and vapor inlet and outlet conduits and a liquid overflow at 1 liter of volume is charged 600 grams of acetic acid, 14 grams tellurium dioxide, 26 grams of 48 percent hydrobromic acid and 28 grams 2-bromoethyl acetate. The oxidizer is gradually heated to 160° C. and 334 grams per hour of a liquid mixture of the following composition is pumped into the reactor: 89.8 percent acetic acid, 2.1 percent tellurium dioxide, 3.9 percent of 48 percent hydrobromic acid and 4.2 percent 2-bromoethyl acetate. The reaction zone is maintained at 400 psig. with an ethylene flow rate of 500 liters (standard conditions) per hour and an oxygen flow rate of 50 liters (standard conditions) per hour. Steady state operation is achieved after about 12 hours. An overflow rate of 442 grams per hour of effluent is collected which is found to contain ethylene glycol diacetate, ethylene glycol monoacetate and ethylene glycol in the following percentages: 27.9% diacetate, 16.5% monoacetate, 2.1% ethylene glycol.

2000 grams of this effluent is subjected to a flash distillation performed at 1 mmHg up to a maximum pot temperature of 100° C. to leave behind the residue. The residue weighs 61.4 grams and contains about 0.8 percent ethylene glycol diacetate and 0.32 percent ethylene glycol monoacetate. The carbon content is 30.7 percent. The volatiles are subjected to a careful distillation with the monoacetate and ethylene glycol being completely esterified to the diester.

25 grams of the residue was mixed with 125 grams of water and allowed to react at 160° C. for 2 hours under 200 psig. nitrogen. Following the two the two hours, 6.7 percent ethylene glycol was found in the mixture by gas chromatographic analysis.

The precursor light components, such as 1,2 dibromoethane, ethylene bromohydrin and 2-bromoethyl acetate when reactead with water yield ethylene glycol.

The embodiments of the invention in which an exclusive property is claimed are defined as follows:

1. In a process for preparing vicinal glycol mono- and diesters of olefins which comprises contacting an olefin containing 2 to 30 carbon atoms and a molecular oxygen containing gas in an oxidation zone with a carboxylic acid containding 2 to 6 carbon atoms in the liquid phase in the presence of a halogen selected from the group consisting of bromine, and a bromine-containing compound capable of producing bromide ions in solution in the oxidation zone, and a variable metal cation selected from the group consisting of tellurium, cerium, antimony, manganese, vanadium, gallium, arsenic, cobalt, copper, selenium, chromium and silver, and a liquid effluent is continuously removed from said oxidation zone, the improvement which comprises separating from said effluent a residue having a higher boiling point than said mono- and diesters, and contacting said residue with water to produce additional vicinal glycol of said olefin.

2. In a process for preparing vicinal glycol mono- and diesters of olefins which comprises contacting an olefin containing 2 to 30 carbon atoms and a molecular oxygen containing gas in an oxidation zone with a carboxylic acid containing 2 to 6 carbon atoms in the liquid phase in the presence of a halogen selected from the group consisting of bromine and a bromine-containing compound capable for producing bromide ions in solution in the oxidation zone, and a variable valent metal cation selected from the group consisting of tellurium, cerium, antimony, manganese, vanadium, gallium, arsenic, cobalt, copper, selenium, chromium and silver, and a liquid effluent is continuously removed from said oxidation zone, the improvement which comprises
 separating from said effluent a stream comprising precursor light components contained in said effluent and having lower boiling points than said mono- and diesters, and
 contacting said precursor light components with water to produce additional vicinal glycol of said olefin.

3. A process for preparing vicinal glycol mono- and diesters of olefins by contacting a vapor feed of an olefin containing 2 to 30 carbon atoms and a molecular oxygen containing gas in an oxidation zone with a carboxylic acid containing 2 to 6 carbon atoms in the liquid phase in the presence of a halogen selected from the group consisting of bromine and bromine-containing compound capable of producing bromide ions in solution in the oxidation zone and a variable valent metal cation selected from the group consisting of tellurium, cerium, antimony, manganese, vanadium, gallium, arsenic, cobalt, copper, selenium, chromium, and silver, and a liquid effluent is continuously removed from said oxidation zone, the improvement which comprises:
 separating from said effluent a residue having a higher boiling point than said mono- and diesters,
 separating from said effluent said carboxylic acid contained in said effluent,
 separating from said effluent the glycol mono- and diesters,
 separating from said effluent a stream comprising precursor light components contained in said effluent and having a lower boiling point than said mono- and diesters, and
 contacting at least one of said residue and said precursor light components with water at an elevated temperature to produce vicinal glycol of said olefin.

4. In a process for preparing ethylene glycol diacetate and ethylene glycol monoacetate which comprises contacting ethylene and a molecular oxygen containing gas in an oxidation zone with acetic acid in the liquid phase in the presence of a bromine containing compound capable of producing bromide ions in solution in the oxidation zone and tellurium cation, and a liquid effluent is continuously removed from said oxidation zone, the improvement which comprises:
 separating from said effluent a residue having a higher boiling point than said ethylene glycol monoacetate and diacetate,
 separating from said effluent said carboxylic acid contained in said effluent,
 separating from said effluent said ethylene glycol monoacetate and diacetate,
 separating from said effluent a stream comprising precursor light components contained in said effluent, and having lower boiling points than said monoacetate and diacetate, and
 contacting at least one of said residue and said precursor light components with water to produce the ethylene glycol.

5. In a process for preparing vicinal glycol mono- and diesters of olefins which comprises contacting an olefin containing 2 to 30 carbon atoms and a molecular oxygen containing gas in an oxidation zone with a carboxylic acid containing 2 to 6 carbon atoms in the liquid phase in the presence of a halogen selected from the group consisting of bromine, chlorine, a bromine-containing compound and a chlorine-containing compound, said compounds being capable of producing, respectively, bromide ions and chloride ions in solution in the oxidation zone, and a variable valent cation selected from the group consisting tellurium, cerium, antimony, manganese, vanadium, gallium, arsenic, cobalt, copper, selenium, chromium and silver, and a liquid effluent is continuously removed from said oxidation zone, the improvement which comprises:
 separating from said effluent a residue having a higher boiling point than said mono- and diesters, and contacting said residue with water to produce additional vicinal glycol of said olefin.

6. The process of claim 5 wherein said oxidation is maintained at from about 90° C. to about 180° C.

7. The process of claim 5 wherein the olefin is a lower olefin of from 2 to 5 carbon atoms.

8. The process of claim 5 wherein said olefin is ethylene.

9. In a process for preparing vicinal glycol mono- and diesters of olefins which comprises contacting an olefin containing 2 to 30 carbon atoms and a molecular oxygen containing gas in an oxidation zone with a carboxylic acid containing 2 to 6 carbon atoms in the liquid phase in the presence of a halogen selected from the group consisting of bromine, chlorine, a bromine-containing compound and a chlorine-containing compound, said compounds being capable of producing, respectively, bromide ions and chloride ions in solution in the oxidation zone, and a variable valent cation selected from the group consisting of tellurium, cerium, antimony, manganese, vanadium, gallium, arsenic, cobalt, copper, selenium, chromium and silver, and a liquid effluent is continuously removed from said oxidation zone, the improvement which comprises:
 separating from said effluent a stream a comprising precursor light components contained in said effluent, and having lower boiling points than said mono- and diesters, and
 contacting said precursor light components with water to produce additional vicinal glycol of said olefin.

10. A process for preparing vicinal glycol mono- and diesters of olefins by contacting a vapor feed of an olefin containing 2 to 30 carbon atoms and a molecular oxygen containing gas in an oxidation zone with a carboxylic acid containing 2 to 6 carbon atoms in the liquid phase in the presence of a halogen selected from the group consisting of bromine, chlorine, a bromine-containing compound and a chlorine-containing compound, said compounds being capable fo producing, respectively, bromide ions and chloride ions in solution in the oxidation zone and a variable valent cation selected from the group consisting of tellurium, cerium, antimony, manganese, vanadium, gallium, arsenic, cobalt, copper, selenium, chromium and silver, and a liquid effluent is continuously removed from said oxidation zone, the improvement which comprises:

separating from said effluent a residue having a higher boiling point than said mono- and diesters, separating from said effluent said carboxylic acid contained in said effluent, separating from said effluent the vicinal glycol mono- and diesters, separating from said effluent a stream comprising precursor light components contained in said effluent, and having lower boiling points than said mono- and diesters, and contacting at least one of said residue and said precursor light components with water at an elevated temperature to produce vicinal glycol.

* * * * *